United States Patent [19]
Kruse et al.

[11] Patent Number: 5,609,198
[45] Date of Patent: Mar. 11, 1997

[54] APPARATUS FOR MEASURING THE PROPERTIES OF MOLD MATERIALS

[75] Inventors: Ernst O. Kruse, Gottmadingen/Randegg, Germany; Christian Renner, Beringen, Switzerland

[73] Assignee: Georg Fischer Giessereianlagen AG, Schaffhausen, Switzerland

[21] Appl. No.: 360,458

[22] Filed: Dec. 21, 1994

[30] Foreign Application Priority Data

Dec. 23, 1993 [CH] Switzerland .......................... 03842/93

[51] Int. Cl.$^6$ ........................ B22C 9/02; B22C 19/00
[52] U.S. Cl. ........................ 164/150.1; 164/456
[58] Field of Search .................. 164/150.1, 151, 164/456, 4.1, 412

[56] References Cited

U.S. PATENT DOCUMENTS

| 2,561,266 | 7/1951 | Dietert ........................... 164/456 X |
| 2,791,120 | 5/1957 | Dietert et al. .................... 164/456 X |

FOREIGN PATENT DOCUMENTS

| 57-193261 | 11/1982 | Japan ........................... 164/456 |
| 711426 | 1/1980 | U.S.S.R. ........................ 164/456 |
| 1125198 | 11/1984 | U.S.S.R. ........................ 164/456 |

*Primary Examiner*—J. Reed Batten, Jr.
*Attorney, Agent, or Firm*—Bachman & LaPointe, P.C.

[57] ABSTRACT

The apparatus includes a stand having a press, a gas permeability measuring device and a weight measuring device mounted thereon for selectively measuring gas permeability, weight, compressor strength, shear strength, bending strength and other mechanical and physical properties.

8 Claims, 1 Drawing Sheet

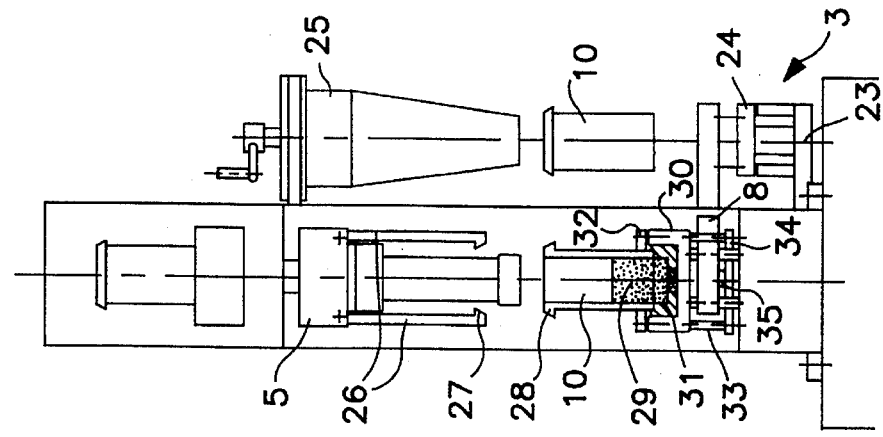
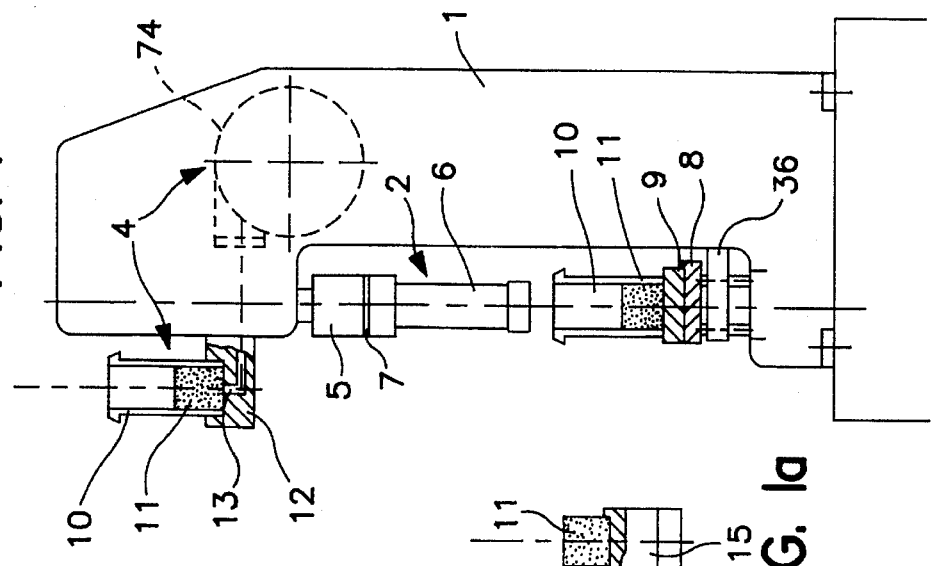

APPARATUS FOR MEASURING THE PROPERTIES OF MOLD MATERIALS

BACKGROUND OF THE INVENTION

The present invention relates to an apparatus for measuring the properties of mold materials including gas permeability, weight, compression strength, shear strength, bending strength and other properties.

Swiss A-646 790 discloses an apparatus of the aforementioned type which is suitable only for the testing of compressive strength, flexural strength, and the compressibility of foundry mold materials.

For judging the properties of mold materials other additional tests and measurements are necessary. For such measurements, such as, for instance, apparent density, test specimen weight, gas permeability, double shear strength, green tensile strength, wet tensile strength, splitting resistance and flexural strength, individual instruments have become known for each test such as described, for instance, in the prospectus: "Test Instruments for Mold and Core Sands" of Georg Fischer Giessereianlagen AG, Bulletin No. GA 293/1a (8/91).

All of these instruments have the disadvantage that they can be used only for one type of test and also in each case give only one measurement value.

Only in the device of Swiss A-646 790 can several measurements be carried out; however, the other measurements or tests mentioned with the other instruments are necessary in order to be able to reliably judge the properties of a foundry mold material.

The object of the present invention is to overcome this disadvantage and to propose a single apparatus of the aforementioned type with which the important mold-material properties of bentonite-bonded and resin-bonded mold materials can be measured and tested. In addition, a reduction in cost and a saving in space in the test laboratory are obtained.

The invention also has the object of determining and recording all data on-line.

SUMMARY OF THE INVENTION

In accordance with the present invention the foregoing objects are achieved by an apparatus of the aforementioned type comprises a stand, press means mounted on said stand, said press means includes a ram, ram actuating means, pressure measuring means and a support for a test piece, gas permeability measuring means mounted on said stand, said gas permeability measuring means includes a gas pressure generator and a pressure drop sensor and weight measuring means including a balance wherein said ram and said support include means adapted to selectively receive one of the following: first means for measuring compression strength, second means for measuring shear strength, third means for measuring bending strength and fourth means for producing test pieces from the foundry molding material.

BRIEF DESCRIPTION OF THE DRAWINGS

The invention is shown in simplified form in the accompanying drawing and will be described below. In the drawing:

FIG. 1 is a side view, with partial sections, of the apparatus for measuring mold-material properties;

FIG. 1a shows the devices for the measurement of the splitting resistance and compressive strength of a test piece;

FIG. 1b shows the devices for the measurement of the double shear strength;

FIG. 1c shows the devices for the measurement of the flexural strength;

FIG. 1d shows the devices for the production of flexure test pieces; and

FIG. 2 is a front view of the apparatus of FIG. 1.

DETAILED DESCRIPTION

The apparatus shown in FIGS. 1 and 2 has a stand 1 on which there are arranged a press device 2, a weight-measuring device 3, and a device 4 for measuring gas permeability. The press device 2 has an actuating drive which can be actuated preferably electrically or else hydraulically or pneumatically, with a press stamp 6, a pressure-measuring device 7 such as, for instance, a piezoelectric gauge which produces electric signals being arranged between the press stamp 6 and the actuating drive 5.

The actuating drive 5 is operatively connected with a weight-measuring device, not shown. The press device 2 has a swing arm 36 which is arranged on the stand 1 and has a support 8 which is developed to receive different support parts. FIG. 1, shows a support part 9 for receiving a sleeve 10 which is filled with the foundry mold material to be tested. The mold material is compressed by the press stamp 6, the measurement of the compressibility being effected by a force measurement and a distance measurement.

The measured compression distance also, at the same time, determines the height of a test piece 11. If it does not have the standard height within a tolerance band, a new one is prepared, with a suitably modified amount of mold material.

The device 4 for measuring the gas permeability has a support plate 12 which is arranged on the stand 1 and has a nozzle 13 which is operatively connected to a gas pressure generator 14, preferably a compressed-air-generator, which is arranged in or on the stand 1. For measuring the gas permeability, the test piece 11 is placed with the sleeve 10 on the support plate 12, the gas permeability of the compacted mold material being determined by measuring the pressure drop with suitable means known in the art.

For the testing of the splitting resistance and the compressive strength, a support part 15, which can be noted from FIG. 1a, which bears the test piece 11 is placed on the support 8 of the stand, the measurement being effected in the pressure-measuring device 7 upon destruction of the test piece 11 by the press stamp 6.

FIG. 1b shows a second support part 16 for the test piece 11 for placing on the support 8, and a shearing stamp 17 for attachment to the stamp 6, these parts being developed for measuring the double shear strength.

For the measuring of the flexural strength on a bar-shaped test piece 18, consisting preferably of core sand or synthetic-resin sand, a support 19 shown in FIG. 1c is fastened on the stand 1 and a bending-compressing stamp 20 is fastened on the stamp 6.

Test bars 18 are produced by the multiple press stamp 21 shown in FIG. 1d and the corresponding press mold 22, which can also be placed on the stamp 6 and the stand 1 respectively. The press stamp 21 and the press mold 22 can also be developed as single stamp and single mold.

The weight-measuring device 3 has, on the side of the stand 1, a balance 23 above the support table 24 of which a filling hopper 25 is arranged on the stand 1. The sleeve is swung, together with its support part 9, by the swing arm 36 onto the balance 23 below the filling hopper 25.

The sleeve 10 which is completely filled with mold material, is weighed, whereby its apparent density can be determined.

After the compacting, the actual length is measured and the compressibility thus determined. From the difference between actual length and standard length of the test piece 11 and the apparent density, the desired weight for the round standard test piece of bentonite-bonded mold material is calculated. This corresponds to the so-called test-piece weight.

As can also be noted from FIG. 2, swingable gripping devices 26 are arranged on the press device 2 or its actuator drive 5 alongside the press stamp 6, these gripping devices having pull hooks which can engage under projections 28 on the sleeve 10.

For the measuring of the tensile strength, a test piece 29 having an end portion which becomes larger in diameter is necessary. For this purpose, the sleeve 10 is placed over a bottom part 30 having an undercut hollow space 31 and placed on the support 8.

Mold material is introduced into the sleeve 1 and the bottom part 30, the test piece 29 being produced by compacting by means of the press stamp 6. A stop plate 32 arranged above the bottom part 30 is connected by rods 33 to a yoke 34 arranged below the support 8, a pressure-measuring device 35 being arranged between the yoke 34 and the support 8.

For measuring the green tensile strength and the wet tensile strength, the gripping devices 26 are lowered until their pull hooks engage in the projections 28 of the sleeve 10.

The sleeve 10, together with the bottom part 30 and the test piece 29, is then pulled upward by means of the actuator drive 5. After the bottom part 30 has come against the stop plate 32, the test piece 39 is stressed in tension. The yoke 35 is, in this connection, pressed via the displaceable bars 33 against the stationary pressure-measuring device 35, whereby the tensile force until reaching the tensile strength upon rupture of the test piece 29 is measure.

For measuring the wet tensile strength, a heatable bottom part 30 is used, whereby the heating process of the mold upon the casting is simulated. In the condensation zone produced thereby, the strength of the mold material decreases.

The measured values found are fed to a evaluating device in the form of electric signals and displaced and/or printed out there.

By the simple, manually operable device described, all necessary measurements or tests can be effected on mold material test pieces, a simple and rapid re-equipping of the device for the different measurements being assured. All movements which influence the measurement (compacting process, testing process) are driven by motor; the speed cannot be changed by the operator. All measurement values are detected on-line.

Since only one device with one evaluation and display unit is necessary for all measurements, the investment costs are low and little space is required.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

We claim:

1. An apparatus for measuring mechanical and physical properties of foundry molding material comprises:

a stand;

press means mounted on said stand, said press means includes a ram, ram actuating means, pressure measuring means and a support for a test piece;

gas permeability measuring means mounted on said stand, said gas permeability measuring means includes a gas pressure generator and a pressure drop sensor; and weight measuring means including a balance wherein said ram and said support include means adapted to selectively receive one of the following: first means for measuring compression strength, second means for measuring shear strength, third means for measuring bending strength and fourth means for producing test pieces from the foundry molding material.

2. An apparatus according to claim 1 wherein the second means comprises a shear stamp having a support part, the third means comprises a bending-compressing stamp having a support part for a bar-shaped test piece (18), the fourth means comprises a press stamp having a corresponding press mold for the production of test pieces.

3. An apparatus according to claim 1 wherein the weight-measuring means includes a filling hopper and a balance for measuring the weight of the molding material.

4. An apparatus according to claim 1 wherein the gas permeability measuring means includes a support plate provided with a nozzle (13) for receiving the test piece, the nozzle being operatively connected with a gas-pressure generator wherein the pressure drop sensor measures the gas permeability of the test piece.

5. An apparatus according to claim 1 wherein the press means includes gripping means comprising hooks which can engage projections on a sleeve holding the test piece.

6. An apparatus according to claim 5 wherein the support includes a bottom part provided with an undercut hollow space, said bottom part, together with a sleeve for holding the test piece mounted thereon, form the mold for the production of a test piece for measuring the green tensile strength.

7. An apparatus according to claim 6 including heating means for heating the bottom part.

8. An apparatus according to claim 6 including means for vertically displacing the bottom part against a stop plate by means of the gripping devices which engage into the sleeve, a yoke which is connected to the stop plate being adapted to be pressed against a pressure-measuring device, arranged fixed in position, for measuring the tensile strength.

* * * * *